Figure 1:
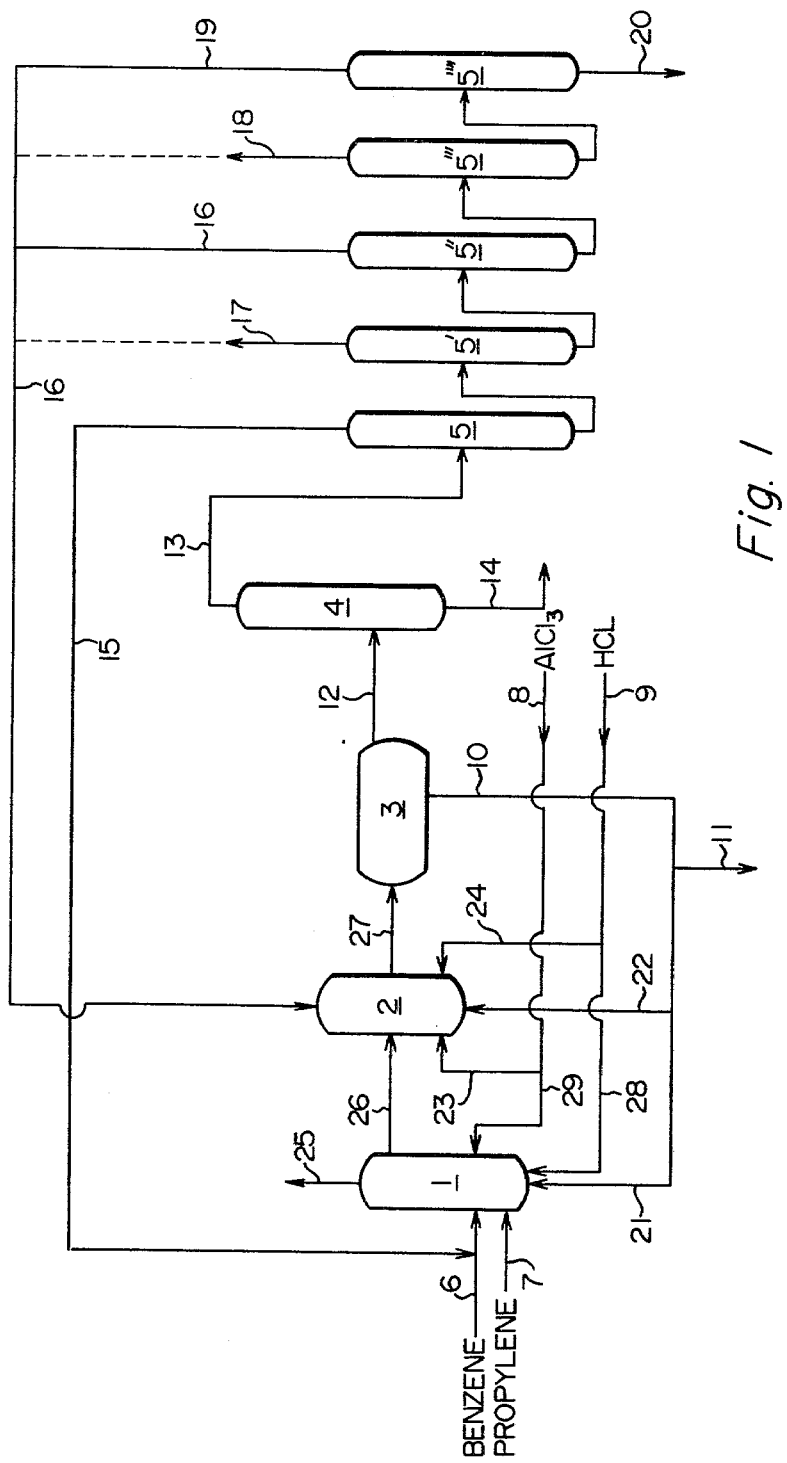

United States Patent [19]

Miki

[11] 4,347,393

[45] Aug. 31, 1982

[54] PROCESS FOR CONTINUOUS PRODUCTION OF CUMENE AND/OR DIISOPROPYLBENZENE

[75] Inventor: Hisaya Miki, Ichihara, Japan

[73] Assignee: Mitsui Petrochemical Industries, Ltd., Tokyo, Japan

[21] Appl. No.: 294,204

[22] Filed: Aug. 19, 1981

[30] Foreign Application Priority Data

Aug. 22, 1980 [JP]  Japan ............................... 55-114818

[51] Int. Cl.$^3$ ........................... C07C 2/70; C07C 5/22
[52] U.S. Cl. ................................... 585/323; 585/459; 585/470
[58] Field of Search ........................ 585/323, 459, 470

[56] References Cited

U.S. PATENT DOCUMENTS

| | | | |
|---|---|---|---|
| 2,817,688 | 12/1957 | Enos | 585/459 |
| 3,126,421 | 3/1964 | Jones | 585/323 |
| 3,306,943 | 2/1967 | Sulo et al. | 585/459 |
| 3,578,722 | 5/1971 | Fraser | 585/459 |
| 4,008,290 | 2/1977 | Ward | 585/323 |

*Primary Examiner*—Curtis R. Davis
*Attorney, Agent, or Firm*—Sherman & Shalloway

[57] ABSTRACT

In a process for producing cumene and/or diisopropylbenzene which comprises, in combination, (I) an alkylating step,
(II) a transalkylating step,
(III) a catalyst separating step,
(IV) a neutralization step, and
(V) fractionally distilling step;

characterized in that (a) step (I) is carried out at a temperature of about 40° C. to about 85° C. while maintaining the activity coefficient (M) of the catalyst at about $10 \times 10^{-4}$ to about $300 \times 10^{-4}$ and the concentration of aluminum chloride in the system at 0.005 to 0.15 mole/liter, and (b) step (II) is carried out without removing the catalyst from the reaction product of step (I) and at a temperature of about 40° C. to about 75° C. in the presence of added fresh aluminum chloride in an amount of 2 to 20 parts by weight/hr per 1000 parts by weight/hr of diisopropylbenzene in the reaction system while maintaining the activity coefficient (M) of the catalyst in the system at about $30 \times 10^{-4}$ to about $300 \times 10^{-4}$ and the concentration of aluminum chloride in the system at 0.3 to 1 mole/liter.

1 Claim, 1 Drawing Figure

PROCESS FOR CONTINUOUS PRODUCTION OF CUMENE AND/OR DIISOPROPYLBENZENE

This invention relates to an improvement in a process for continuously producing cumene and/or diisopropylbenzene, which comprises, in combination, a step of alkylating benzene with propylene, a step of transalkylation between the reaction product of the alkylating step and recycle isopropylbenzene compounds from a distillation step mentioned below, a step of separating and removing the liquid aluminum chloride complex catalyst from the reaction product, a step of neutralizing the transalkylation product from which the catalyst has been removed, and a step of fractionally distilling the neutralization product to recover cumene and/or diisopropylbenzene and recycling the remaining isopropylbenzene compounds to the transalkylation step.

When the production of cumene is intended, the process of the invention has the advantage that the amount of by-product ethylbenzene which is likely to cause formation of by-product acetaldehyde can be decreased and the process can be performed with a reduced amount of catalyst consumed. The by-product acetaldehyde is an unwanted compound because it reduces the quality of acetone formed by acid cleavage of the oxidation reaction product. When the production of m-diisopropylenzene is intended, the process has the advantage that the amount of by-product trimethylindane which is difficult to separate from m-diisopropylbenzene can be decreased, and the process can be performed with a reduced amount of catalyst consumed. Furthermore, when it is desired to produce p-diisopropylbenzene, the process has the advantage that the amount of by-product hexylbenzene which is difficult to separate from p-diisopropylbenzene can be decreased, and the process can be performed with a reduced amount of catalyst consumed. The process of the invention can thus achieve an excellent improvement in the continuous industrial production of cumene and/or diisopropylbenzene.

More specifically, this invention pertains to an improved process for producing cumene and/or diisopropylbenzene which comprises, in combination, (I) an alkylating step of reacting benzene with propylene in the presence of a liquid aluminum chloride complex catalyst, (II) a transalkylating step of reacting the reaction product of step (I) containing the complex catalyst with recycle isopropylbenzene compounds from a distillation step (V) stated below in the presence of added fresh aluminum chloride and hydrogen chloride in a reaction zone different from the reaction zone of step (I), (III) a catalyst separating step of separating the liquid aluminum chloride complex catalyst from the transalkylation product of step (II) in a zone different from the zone of step (II) and recycling the separated catalyst to step (I) and/or step (II), (IV) a neutralization step of neutralizing the transalkylation product of step (III) with an alkali in a zone different from the zone of catalyst separating step (III), and (V) fractionally distilling the neutralization product of step (IV) in a zone different from the zone of step (IV) to recover the cumene fraction and/or the diisopropylbenzene fraction and recycling the remaining isopropylbenzene compounds to step (II); characterized in that (a) step (I) is carried out at a temperature of about 40° C. to about 85° C. while maintaining the activity coefficient (M) of the catalyst at about $10\times10^{-4}$ to about $300\times10^{-4}$ and the concentration of aluminum chloride in the system at 0.005 to 0.15 mole/liter, and (b) step (II) is carried out without removing the catalyst from the reaction roduct of step (I) and at a temperature of about 40° C. to about 75° C. in the presence of added fresh aluminum chloride in an amount of 2 to 20 parts by weight/hr per 1000 parts by weight/hr of diisopropylbenzene in the reaction system while maintaining the activity coefficient (M) of the catalyst in the system at about $30\times10^{-4}$ to about $300\times10^{-4}$ and the concentration of aluminum chloride in the system at 0.3 to 1 mole/liter.

A process for continuous production of cumene and/or diisopropylbenzene is known which comprises (I) an alkylating step of reacting benzene with propylene in the presence of a liquid aluminum chloride complex catalyst formed by supplying aluminum chloride to the reaction system to form an alkylation product mainly containing cumene, diisopropylbenzenes (m- and p-), polyisopropylbenzenes such as triisopropylbenzene, the unreacted benzene and the complex catalyst, (II) a transalkylation step of transalkylating the alkylation product with recycle isopropylbenzene compounds from a distillation step (V) in the presence of added fresh aluminum chloride and hydrogen chloride in a rection zone different from the zone of step (I), (III) a step of separating and removing the liquid aluminum chloride complex catalyst from the transalkylation product of step (II) in a zone different from the transalkylation step (II), (IV) a step of neutralizing the transalkylation product with an alkali in a zone different from the zone of step (III), and (V) a distillation step of fractionally distilling the neutralization product from step (IV) in a zone different from the zone of the neutralization step (IV) to recover at least one fraction selected from cumene and diisopropylbenzenes and recycling the remaining isopropylbenzene compounds other than the distillation bottoms to step (II).

When the cumene fraction is to be recovered in step (V), remaining components other than the distillation bottoms, for example a benzene fraction, are recycled to step (I) and/or step (II) and polyisopropylbenzene fractions such as diisopropylbenzene or triisopropylbenzene are recycled to step (II). When it is desired to recover a diisopropylbenzene fraction, remaining components other than the distillation bottoms, such as the benzene fraction and a part of the cumene fraction, are recycled to step (I) and/or step (II) and polyisopropylbenzene fractions such as cumene and triisopropylbenzene, to step (II).

One example of this known continuous process is disclosed in British Pat. No. 773,502 (corresponding to Japanese Patent Publication No. 7069/1957).

The British patent provides a process for the production of alkylated aromatic hydrocarbons which comprises reacting an aromatic hydrocarbon or hydrocarbons, in a first reaction stage in the liquid phase at 5° to 100° C. with an olefine or an alkyl halide in the presence of a liquid complex catalyst for alkylation comprising a strongly active Friedel Crafts catalyst, at least some hydrogen halide, and an alkylated aromatic hydrocarbon and which is immiscible with the starting hydrocarbon and products, to give a mixture containing at least mono- and di-alkylated hydrocarbons, parting this mixture from the liquid catalyst complex and subjecting the mixture without substantial addition of other reactants in a second reaction stage in the liquid phase to a temperature of 5° to 100° C. in the presence of a further quantity of a similar complex catalytic for alkylation and immiscible with the starting hydrocarbon and products, whereby isomerization and interalkylation occur, parting the mixed product from the liquid catalyst complex, and recovering the desired alkylated aromatic hydrocarbon or hydrocarbons from the mixed product by a fractional separation.

The British patent states: "In a continuous process, in either stage, it is preferred to draw off a mixture of the two liquid phases continuously from the reactor, lead this mixture continuously to a decanter, continuously decant off the top, that is the product layer, and pass it to the next stage in the process, and continuously decant off the bottom layer of catalyst complex. The layer of catalyst complex from the second stage decanter is cycled to the first stage reactor and the layer of catalyst complex from the first stage decanter is discarded." Thus, in this Patent, it is recommended in employing a continuous process to cycle the catalyst from step (II) to step (I) and to provide a step of removing the catalyst between steps (I) and (II).

It is know that in the continuous production of cumene and/or diisopropylbenzene from benzene and propylene by a process comprising a combination of steps (I) to (V), aluminum chloride in the reaction system forms a liquid aluminum chloride complex catalyst and the catalytic activity of the complex catalyst decreases with time. The present inventors tried to use the complex catalyst repeatedly by using the complex used in the alkylation step together with the product in the transalkylation step, separating the complex from the reaction product of the transalkylation step, and recycling the complex to the alkylation step. Consequently, they ascertained that the activity of the complex catalyst decreased upon repeated use in the alkylation or the transalkylation reaction. In order, therefore, to maintain the activity of the complex catalyst and the yield per unit time of cumene and/or diisopropylbenzene at certain levels, it is necessary to discharge a part of the complex catalyst having reduced activity and freshly supply aluminum chloride and hydrogen chloride as a promoter, thereby preventing an undue reduction in catalytic activity.

It is generally known on the other hand that in the production of cumene and/or diisopropylbenzene by a combination of the alkylating step and the transalkylating step, trimethylindane and ethylbenzene are formed as by-products. Formation of a large quantity of by-product ethylbenzene is industrially disadvantageous in that because its boiling point is relatively close to that of cumene, a special distillation column for removing ethylbenzene is required to obtain cumene of high impurity.

Formation of by-product trimethylindane also has the disadvantage that because its boiling point is very close to that of m-diisopropylbenzene, it is industrially impossible to separate it from m-diisopropylbenzene by distillation, and therefore, the purity of m-diisopropylbenzene, if it is the desired product, is reduced.

Investigations of the present inventors have shown that when m-diisopropylbenzene is recycled to the transalkylation step, the amount of by-product ethylbenzene further increases because of trimethylindane contained in the m-diisopropylbenzene.

The formation of by-product hexylbenzene also occurs, and therefore, a number of troubles exist in order to perform the process for continuous production of cumene and/or diisopropylbenzene by the combination of steps (I) to (V).

The present inventors have made extensive investigations in order to develop an industrially advantageous process for continuous production of cumene and/or diisopropylbenzene by a combination of steps (I) to (V). These investigations have led to the discovery that the activity coefficient (M) of the catalyst, the concentration of aluminum chloride in the reaction system and the reaction temperature in each of the alkylating step (I) and the transalkylating step (II), taken together, are important parameters which will be conducive to elimination of the many troubles mentioned above.

The present inventors have studied these parameters in detail, and found that the above troubles can be advantageously avoided by performing a combination of steps (I) to (V) under conditions (a) and (b) in combination.

It has specifically been found that cumene and/or diisopropylbenzene can be produced from benzene and propylene with industrial advantage by performing the continuous process consisting of the combination of steps (I) to (V) under the following conditions in combination.

(a) The alkylation step (I) is carried out (a-1) while maintaining the activity coefficient (M) of the catalyst at about $10 \times 10^{-4}$ to about $300 \times 10^{-4}$ and the concentration of aluminum chloride in the system at 0.005 to 0.15 mole/liter, and (a-2) at a temperature of about 40° to about 85° C.

(b) The transalkylation step (II) is carried out (b-1) without removing the catalyst from the reaction product of step (I), (b-2) in the presence of added fresh aluminum chloride in an amount of 2 to 20 parts by weight/hr per 1000 parts by weight/hr of diisopropylbenzene in the reaction step, (b-3) while maintaining the activity coefficient (M) of the catalyst in the system at about $30 \times 10^{-4}$ to about $300 \times 10^{-4}$ and the concentration of aluminum chloride in the system at 0.3 to 1 mole/liter, and (b-4) at a temperature of about 40° to about 75° C.

It is an object of this invention to provide an improved process for continuously producing cumene and/or diisopropylbenzene from benzene and propylene with commercial advantage.

The above and other objects and advantages of the invention will become more apparent from the following description.

A preferred example of the catalyst containing aluminum chloride as an essential ingredient used in steps (I) and (II) of the process of the invention is a complex catalyst prepared from 1 mole of aluminum trichloride, 0.3 to about 4 moles of hydrogen chloride as a promoter, and an aromatic hydrocarbon such as benzene and cumene.

It is known that contacting of aluminum trichloride, hydrogen chloride and an aromatic hydrocarbon results in an oily complex having a high specific gravity and a complex structure. The liquid aluminum chloride catalyst formed forms a phase different from an aromatic hydrocarbon phase of low specific gravity. The resulting complex functions as a catalyst for alkylation and transalkylation.

In the process of this invention, the alkylation reaction step (I) of reacting benzene and propylene in the presence of the liquid aluminum chloride complex catalyst is carried out at a temperature of about 40° to about 85° C. while maintaining the activity coefficient (M) of the catalyst at about $10 \times 10^{-4}$ to about $300 \times 10^{-4}$ and the concentration of aluminum chloride in the system at 0.005 to 0.15 mole/liter [requisite (a)]. Furthermore, in the process of the invention, the transalkylation step (II) of reacting the reaction product from step (I) containing the complex catalyst with recycle isopropylbenzene compounds from the distilation step (V) in the presence of added fresh aluminum chloride and hydrogen chloride in a reaction zone different from the reaction zone of step (I) is carried out without removing the complex catalyst from the reaction product of step (I) and at a temperature of about 40° C. to about 75° C. in the presence of 2 to 20 parts by weight/hr, per 1000 parts by weight/hr of diisopropylbenzene in the reaction system, of freshly added aluminum chloride while maintaining the activity coefficient (M) of the catalyst in the system at about $30 \times 10^{-4}$ to about $300 \times 10^{-4}$ and the concentration of aluminum chloride in the system at 0.3 to 1 mole/liter [requisite (b)].

In the performance of the process of this invention, step (II) is carried out without removing the complex catalyst from the reaction product of step (I). The transalkylation is carried out in the presence of 2 to 20 parts by weight/hr, per 1000 parts by weight/hr of diisopropylbenzene, of freshly added aluminum chloride together with hydrogen chloride.

There is preferably employed an embodiment in which the liquid complex catalyst is separated from the reaction product of step (II), and the separated liquid complex catalyst is recycled to step (I) and/or step (II). The liquid complex catalyst in an amount which balances with the freshly added aluminum chloride and hydrogen chloride can be drawn off out of the system from the aforesaid recycle lines. Aluminum chloride and hydrogen chloride may also be added to step (I).

By partly removing the liquid complex catalyst to be recycled and adding fresh aluminum chloride and hydrogen chloride, the activity coefficient (M) of the complex catalyst is maintained at about $10 \times 10^{-4}$ to about $300 > 10^{-4}$ in the alkylation step (I), and about $30 \times 10^{-4}$ to about $300 \times 10^{-4}$ in the transalkylation step (II).

The activity coefficient (M) is defined as a value obtained by the following measuring method.

p-Diisopropylbenzene and benzene are mixed so that the mole ratio of the isopropyl groups to the benzene ring is precisely 0.6. 200 ml of the mixture is charged into a reactor having a capacity of about 500 ml and equipped with a stirrer. While maintaining the mixture at 50° C., dry hydrogen chloride gas under atmospheric pressure is blown into the reactor at a rate of about 300 ml/min. The mixture is allowed to stand for about 30 minutes with stirring to saturate the mixture with hydrogen chloride. A cooling reflux device is provided at an outlet line for hydrogen chloride gas so that benzene and p-diisopropylbenzene may not dissipate out of the system in this operation. Subsequently, 10 ml of the liquid complex catalyst is added dropwise to the reactor, and while maintaining a temperature of 50° C., blowing of hydrogen chloride gas is continued at a rate of about 10 ml/min. After the addition of the complex, the reaction mixture is sampled 5 to 10 times every 30 seconds to 1 minute. The samples are treated in the following manner to remove the catalyst. Specifically, each of the samples was washed with a 2% aqueous solution of sodium hydroxide and then with water, and dehydrated over anhydrous sodium sulfate. The above treatment is carried out carefully so as not to evaporate off volatile components such as benzene.

The samples so treated are then analyzed by gas chromatography for the amont of cumene, and the concentration of cumene $[CU]_i$ where the subscript i means a value for the sample at time ti.

Yi is calculated in accordance with equation (I).

$$Y_i = \frac{(CU)_e}{2(DIPB)_o} \times l_n \left( \frac{(CU)_e}{(CU)_e - (CU)_i} \right) \quad (I)$$

Subsequently, the sampling time ti (minutes) and $Y_i$ (wherein i=1–10) are caused to approximate the following linear equation (II).

$$Y = Mt + C \quad (II)$$

M is calculated by the method of least squares.

In equation (I), $[CU]_e$ is the equilibrium concentration of cumene, and $[DIPB]_o$ is the concentration of p-diisopropylbenzene in the mixture of benzene and p-diisopropylbenzene before addition of the complex. The concentrations are expressed in moles/liter, and the unit of M is $minute^{-1}$. Accordingly, $[DIPB]_o$ is 2.5 moles/liter.

When benzene, cumene, diisopropylbenzene, etc. are mixed in the presence of the complex catalyst, transalkylation takes place and finally the proportions of benzene, cumene, o-diisopropylbenzene, m-diisopropylbenzene, p-diisopropylbenzene, and triisopropylbenzene reach a thermodynamic equilibrum. The concentration of cumene at this time is defined as the equilibrium concentration of cumene. The equilibrium concentration of cumene varies depending upon the mole ratio of the isopropyl groups to the benzene ring in the starting reactant mixture and also upon the temperature. In the present invention, $[CU]_e = 3.62$ moles/liter is applied to equation (I).

The M value so determined shows a positive correlation with the constant K of the rate of reaction in the transalkylation represented by the formula (III) below.

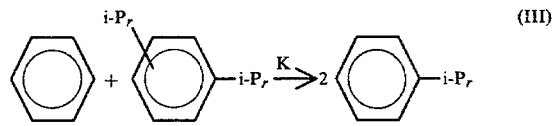

(III)

Larger M values show a higher catalytic activity of the complex catalyst.

In a process for producing cumene and/or diisopropylbenzene, there exists an equilibrium composition determined definitely by the mole ratio of the isopropyl groups to the benzene ring, and the reaction conditions, such as the reaction temperature, the reaction time (residence time), the concentration of the catalyst and the catalytic activity (M value), are operating factors which determine how quickly this equilibrium composition is reached. That the reaction solution (the solution at the outlet of the transalkylation reactor) reaches an equilibrium concentration means that the conversion to products containing isopropyl groups, such as cumene and diisopropylbenzene, is high, and the amount of benzene to be recycled is small. Thus, the time and labor required in a separating and purifying step such as distillation can be reduced.

In order to obtain the equilibrium composition of the reaction mixture, the reaction temperature is increased to increase the rate of the reaction. If moderate conditions are selected to obtain a moderate rate of reaction, the reaction time becomes very long. At high temperatures, the amount of by-products formed excessively increases to reduce the purity and yield of the final product. Under the moderate conditions, the residence time is prolonged. Hence, a reactor of a large volume is required, and expenditures that go into the equipment increase greatly.

Investigations of the present inventors have shown that if the difference of the concentration of cumene from the equilibrium concentration of cumene is larger, the rate of the reaction is faster, and if the difference is smaller, the rate of the reaction is slower. Naturally, when the equilibrium composition is reached, the apparent rate of the reaction is zero, and even under moderate conditions, by-products are formed to reduce the purity and yield of the final product.

If the reduction of the time and labor during distillation is considered, the composition of the reaction mixture is preferably as close as possible to the equilibrium composition, but this is not always necessary. In order to reduce expenditures for the reactor, etc., that range of the moderate reaction conditions which increases the rate of the reaction is desirably selected, and a region slightly out of the equilibrium compositions is preferred. For this purpose, the concentration of cumene in the reaction mixture is preferably 65 to 99%, more preferably 75 to 95%, of the equilibrium concentration of cumene (the equilibrium attaining ratio). If the equilibrium attaining ratio of cumene is maintained as above mentioned, a variation in the concentration of cumene is noted with even a slight fluctuation in the reaction conditions. For example, if the concentration of cumene decreases with the reaction temperature, the residence time and the concentration of the catalyst being constant, the activity (M) of the catalyst decreases. In this case, it is possible to control the M value of the catalyst to a right value by adding $AlCl_3$ and bringing the equilibrium attaining ratio of cumene to the desired one.

When in the production of diisopropylbenzene alone as a product, cumene is recycled dividedly to the alkylater and the transalkylater, the concentration of cumene in the transalkylater may exceed the equilibrium value depending upon the ratio of the cumene in these reactors. In this case, too, the rate of the reaction is faster as the difference of the concentration of cumene from the equilibrium concentration of cumene is larger, and it is preferred to operate under such conditions that the concentration of cumene in the reaction mixture does not reach its equilibrium concentration.

Water or a sulfur-containing compound contained in the starting materials, or by-product indanes, indenes or high-boiling substances are the cause of reduced catalytic activity. The activity of the catalyst is reduced abruptly or gradually by the inclusion or accumulation of these compounds in unusual amounts. The concentration of cumene is high as compared with the concentrations of other isopropyl-containing products, and can be a suitable factor for judging the reduction of catalytic activity.

The steps (I) and (II) in the process of this invention are carried out so as to meet the activity coefficient (M) in the requisites (a) and (b).

By adjusting the M value of the complex catalyst in each of the above step to the values described in (a) and (b), the yield per unit time of cumene and/or diisopropylbenzene can be adjusted to a value suitable for industrial production and the cost of catalyst preparation can be reduced. If the M value is too high, the complex catalyst does have high catalytic activity, but large amounts of aluminum chloride and hydrogen chloride should be freshly added. If the M value is too small, the catalytic activity is low and the yield per unit time of the product is small.

The M value of the complex catalyst can be adjusted to the above-specified range by the amount of the complex catalyst discharged out of the reaction system and the amounts of freshly added aluminum chloride and hydrogen chloride gas. The quantitative relation of these varies depending upon other reaction conditions such as the rection temperature.

The steps (I) and (II) of the process of the invention are also carried out while maintaining the concentration of aluminum chloride at the specified values shown in (a) and (b) the requisites (a) and (b). If in step (I), the concentration of aluminum chloride falls below 0.005 mole/liter, the activity of the catalyst is reduced by a trace of water contained in benzene and high-boiling compounds formed as by-products in small amounts, and propylene cannot be fully absorbed. If, on the other hand, the concentration of aluminum chloride exceeds 0.15 mole/liter, the amounts of undesirable by-products such as ethylbenzene, trimethylindane and hexylbenzene increase and the amounts of by-product high-boiling products also increase to reduce the yield of the final desired product. If in step (II) the concentration of aluminum chloride is lower than 0.3 mole/liter, the conversion to the final product such as cumene or diisopropylbenzene is reduced, and the time and labor required for purification of the product increase. If the concentration of aluminum chloride exceeds 1 mole/liter, by-products such as ethylbenzene, trimethylindane, hexylbenzene and high-boiling by-products increase to reduce the yield of the final product.

In step (I) and (II), the reaction system separates upon standing into a layer having a high specific gravity containing the liquid aluminum chloride catalyst and a layer of a lower specific gravity containing aromatic hydrocarbons. In the hydrocarbon layer, aluminum chloride is present in an amount of about 50 to about 200 ppm as Al atom. In the present invention, the concentration of aluminum chloride denotes the concentration of aluminum chloride including that contained in the hydrocarbon layer.

In the process of this invention, it is also essential that steps (I) and (II) be carried out at the temperatures specified in the requisites (a) and (b).

In the alkylation step (I) of the process of this invention, propylene is reacted with benzene in the presence of the complex catalyst to form cumene, diisopropylbenzene, triisopropylbenzene, teeraisopropylbenzene, etc. The performance of step (I) at a temperature of about 40° to about 85° C. is one important requisite for achieving the objects of this invention when taken together with the specified activity coefficient (M) of the complex catalyst and the reaction temperature condition in the transalkylation step (II). If the reaction temperature is lower than 40° C., the rate at which benzene and propylene are reacted to form cumene is reduced. Furthermore, the degree of reduction of the rate at which the resulting cumene reacts further with propylene to form diisopropylbenzene or polyisopropylbenzenes is less than the degree of the reduction of the rate at which benzene reacts with propylene to form cumene. Hence, the amount of cumene contained in the reaction product of step (I) is small. As a whole, the yield of cumene per unit time decreases. Moreover, because the reaction involving addition of propylene to the benzene ring is very exothermic, a large quantity of a cooling medium is required to control the temperature to a low level. If, on the other hand, the reaction temperature exceeds about 85° C., the amounts of by-product trimethylindane and ethylbenzene increase, and side-reactions such as dimerization or trimerization of propylene take place to form nonane and nonene which are difficult to separate from cumene.

The mole ratio of the amount of propylene fed to step (I) to the total amount of benzene fed freshly into the reaction system and benzene recycled from the distillation step (V), which differs slightly depending upon whether the final desired product is cumene or diisopropylbenzene, is for example, about 0.05 to about 1.1, preferably from about 0.2 to about 1.0. Step (I) can be performed at atmospheric pressure to about 20 kg/cm$^2$.G. The reaction is carried out continuously. The residence time in the reaction zone of step (I) is about 1 minute to about 3 hours, preferably about 10 minutes to about 1 hour.

The composition of the reaction product in step (I) varies depending upon the reaction conditions, but approximately it consists of about 10 to about 90% by weight of benzene, about 10 to about 50% by weight of cumene, about 1 to about 20% by weight of m-diisopropyl benzene, about 0.5 to about 15% by weight of p-diisopropylbenzene, and about 0.01 to about 30% by weight of triisopropylbenzene. When cumene is to be obtained as a product, the proportion of by-product ethylbenzene is about 0.03 to about 0.15% by weight based on the weight of cumene.

The alkylation product of step (I) carried out under condition (a) which contains the complex catalyst is then fed into a reaction zone of the transalkylation step (II) which differs from the reaction zone of step (I).

As specified in the requisite (b), step (II) is carried out without removing the liquid complex catalyst from the reaction product of step (I).

In the transalkylation step (II), the reaction product from the alkylation step (I) is reacted with recycle isopropylbenzene compounds from the distillation step (V). Accordingly, the types and amounts of the recycle isopropylbenzene compounds differ depending upon the fractions recovered in step (V).

When cumene alone is to be obtained as a final product, diisopropylbenzene and triisopropylbenzene are recycled to step (II). When both cumene and m-diisopropylbenzene and p-diisopropylbenzene are to be recovered as the desired product, polyisopropylbenzenes not recovered as the desired product are recycled to step (II). When m-diisopropylbenzene and p-diisopropylbenzene are to be recovered as the desired products, cumene. polyisopropylbenzenes and diisopropylbenzene not recovered as products are recycled to step (II). In recycling cumene, diisopropylbenzene and polyisopropylbenzenes, they may be partly cycled to step (I).

The recycle isopropylbenzene compounds denote remaining components left after recovering the desired fractions in step (V).

The process of this invention is preferably applied when m-diisopropylbenzene is recycled from the distillation step (V), that is when m-diisopropylbenzene is not obtained as the desired product or is obtained in a small amount.

The other important element of the invention is the reaction temperature of step (II). In combination with the specified M values of the complex catalyst and the reaction temperature in step (I), the reaction temperature in step (II) makes it possible to achieve the objects of the invention. Specifically, the transalkylation reaction in step (II) is carried out at a temperature of about 40° to about 75° C. It is essential that the reaction temperature in step (II) should not exceed 75° C. If step (II) is carried out at temperatures above 75° C., the amount of by-product trimethylindane increases, and the purity of m-diisopropylbenzene is reduced if it is the desired product. Furthermore, in recycling a part, or the whole, of m-diisopropylbenzene from step (V) to step (II), the formation of by-product ethylbenzene in step (II) becomes pronounced.

Investigations of the present inventors have shown that the amount of by-product ethylbenzene in step (II) increases as the concentration of trimethylindane in the transalkylation step (II) increases; and that the concentration of trimethylindane in step (II) is determined depending upon the reaction conditions employed but its concentration in a steady state increases with an increase in the reaction temperature in step (II), a decrease in the M value of the catalyst complex catalyst recycled, and with an increase in the amount of m-diisopropyl benzene, which is impossible of separation from trimethylindane, to be recycled from step (V) to step (II).

The complex catalyst used recyclically in this invention has such an a degree of catalytic activity as to withstand industrial practice. If the transalkylation reaction is carried out at a temperature of more than 75° C. (and especially when an operation of recycling m-diisopropylbenzene to step (II) is to be effected), the concentration of trimethylindane in step (II) becomes so large that the amount of by-product ethylbenzone in step (II) cannot be ignored. This leads to a vicious circle in that the performance of the transalkylation step (II) at high temperatures accelerates decreasing of the activity coefficient (M) of the complex catalyst and results in a further increase in the formation of by-product ethylbenzene.

Accordingly, the combination of the activity coefficient (M) of the complex catalyst with the reaction temperature of the transalkylation step (II) is of utmost importance for inhibiting formation of by-product ethylbenzene and trimethylindane, especially ethylbenzene. If step (II) is carried out at a temperature lower than 40° C., the rate of the transalkylation reaction is slow, and the yeilds of cumene and other desired products per unit time are low. The step (II) can be carried out at atmospheric pressure to about 10 kg/cm$^2$.G in a continuous manner, and the residence time is about 10 minutes to about 5 hours, preferably about 30 minutes to about 4 hours.

The composition of the reaction product in step (II) varies depending upon the reaction conditions. Approximately, it consists of about 2 to about 60% by weight of benzene, about 25 to about 55% by weight of cumene, about 2 to about 40% by weight of m-diisopropylbenzene, about 1 to about 20% by weight of p-diisopropylbenzene, about 0.2 to about 30% by weight of triisopropylbenzene and about 0 to about 2% by weight of other high-boiling compounds.

Ethylbenzene as a by-product is small in amount, usually are not more than 0.15% by weight, and at times not more than 0.05% by weight. The amount of by-product trimethylindane is also small, and even when m-diisopropylbenzene is recycled from step (V) to step (II), the amount of trimethylindane accumulated is small.

The transalkylation product obtained by steps (II) in the manner mentioned above is then subjected, in a zone different from the zone of step (II), to a catalyst separating step (III) in which the liquid aluminum chloride complex catalyst is separated from the reaction product and recycled to step (I) and/or (II).

In step (III), the reaction product is separated into an aromatic hydrocarbon phase containing the desired products and a layer of the liquid aluminum chloride complex catalyst having a higher specific gravity by a suitable separating means such as sedimentation by standing or forced separation by centrifugation. The separated catalyst is recycled to step (I) and/or step (II). It is preferred at this time to discharge a part of the catalyst in an amount balanced with the amounts of fresh aluminum chloride and hydrogen chloride added in step (II) and at times in step (II) also and to recycle the remainder.

The transalkylation product from which the catalyst has thus been separated is then subjected to a neutralization step (IV) for neutralizing the transalkylation reaction product of step (III). In step (IV), the transalkylation product from which the catalyst has been separated is neutralized with an alkali to remove the catalyst still remaining in the product. This may be achieved, for example, by contacting the complex dispersed or dissolved in the oil with an alkali such as aqueous NaOH; or by first destroying the complex with water or water containing hydrochloric acid, separating the mixture into an oil layer and a water layer, and then neutralizing hydrogen chloride or aluminum chloride remaining in the oil layer by strongly contacting it mechanically with an alkali such as an aqueous solution of sodium hydroxide. This operation may be carried out in one or a multiplicity of stages.

The neutralization product from the neutralization step (IV) is then fractionally distilled in a zone different from the zone of step (IV) to recover a cumene fraction and/or a diisopropylbenzene fraction, and the remaining isopropylbenzene compounds are recycled to step (II). In the recycling operation, the unreacted benzene is recycled to step (I).

Since the amount of by-product ethylbenzene present in the reaction product of step (II) is small even when all of the m-diisopropylbenzene fraction in step (V) is recycled to step (II), cumene of high purity can be obtained without particularly using a special distillation column for removal of ethylbenzene. Preparation of specially purified cumene can be effected by an easier operation than in the prior art.

Furthermore, since the amount of by-product trimethylindane is small, the purity of m-diisopropylbenzene is high when it is also recovered as the desired product. When only a small amount of the m-diisopropylbenzene fraction in step (V) is to be obtained or when all of the m-diisopropylbenzene fraction is to be obtained intermittently, m-diisopropylbenzene having high purity can be recovered.

The advantages of the present invention are summarized as follows:

In the production of cumene as the desired compound:
1. The yields of cumene and/or diisopropylbenzenes per unit time are sufficient for industrial practice.
2. The cost of catalyst preparation is low.
3. The amounts of by-product ethylbenzene, trimethylindane and hexylbenzene zre small, and high-purity cumene can be obtained without providing a special distillation column for removal of ethylbenzene. m-Diisopropylbenzene and p-diisopropylbenzene of high purity can also be obtained.
4. The amount of by-product ethylbenzene is small even when a technique of recycling the m-diisopropylbenzene fraction to the transalkylation step, which is liable to cause formation of by-product ethylbenzene, is employed.

In the production of m- and/or p-diisopropylbenzene as the desired product:
1. The cost of catalyst preparation is low.
2. The amounts of by-product trimethylindane and hexylbenzene are small, and m-diisopropylbenzene and p-diisopropylbenzene of high purity can be obtained.

The following Examples and Comparative Examples illustrate the present invention more specifically. In these examples, the amounts of the starting materials and reaction products are expressed in parts by weight per unit time.

EXAMPLE 1

330 Parts by weight of benzene dehydrated and recycled from a distillation step 5 in the accompanying drawing (FIG. 1) through a line 15 and 170 parts of fresh benzene supplied through a line 6 were fed into an alkylater 1. The alkylater 1 was also charged with 105 parts of propylene containing 6 parts of propane through a line 7, 23 parts of a liquid aluminum chloride complex catalyst from a catalyst separator 3 through lines 10 and 21, 0.1 part of substantially water-free hydrogen chloride gas intermittently through lines 9 and 28, and 0.05 part of aluminum trichloride through lines 8 and 29. The unreacted propane was discharged out of the reaction system through a line 25. The reaction temperature in the alkylater 1 was set at 79° C.

The reaction product from the alkylater 1 was fed into a transalkylater 2 through a line 26. The transalkylater 2 was also charged with 177 parts of polyisopropylbenzenes such as m-diisopropylbenzene, p-diisopropylbenzene and triisopropylbenzene recycled from distillation steps 5″ and 5‴ through lines 16 and 19, 250 parts of the complex catalyst from the catalyst separator 3 through lines 10 and 22, 0.4 part of substantially water-free hydrogen chloride through lines 9 and 24, and 0.6 part of aluminum trichloride intermittently through lines 8 and 23. The reaction temperature in the transalkylater 2 was set at 64° C.

The reaction product at the transalkylater 2 was supplied to the catalyst separator 3 through a line 27, and a layer of the complex catalyst having a high specific gravity was recycled through a line 10, and a portion (1.1 parts) of this layer was discharged out of the system through a line 11. The oil layer was sent to a washing and neutralization tank 4 where the catalyst component was completely removed. The remainder (776 parts) was fed into the distillation step 5 through a line 13.

In the distillation step, a distillation column for removal of ethylbenzene was not provided, and 240 parts of cumene containing 0.06 part % by weight of ethylbenzene and a purity of more than 99.9% was obtained through a line 17, and 26 parts of p-diisopropylbenzene containing 0.8% by weight of trimethylindane, through a line 18. All (330 parts) of the benzene fraction was recycled to the alkylater 1 through line 15, and all (177 parts) of the remaining p-diisopropylbenzene, m-diisopropylbenzene and triisopropylbenzene fractions were recycled to the transalkylater 2 through lines 16 and 19. 2.5 Parts of high-boiling fractions were discharged through a line 20.

The activity coefficient M of the complex catalyst in the reactors 1 and 2 and the composition of the reaction mixture in line 13 were determined, and the results are shown in Table 1.

EXAMPLE 2

In this Example, different reaction temperatures were used in steps (I) and (II).

Specifically, the procedure of Example 1 was repeated except that the reaction temperature was maintained at 80° C. in the alkylater 1, and at 74° C. in the transalkylater 2.

The activity coefficient M of the complex catalyst was adjusted as shown in Table 1. Since the rates of various reactions which took place within the transalkylater changed depending upon the reaction temperatures, the composition and amount of the mixture circulating through the individual lines inevitably changed. However, by showing the composition of the reaction mixture at line 13, it will be clear in which reaction system the above process was performed.

From the distillation steps 5' and 5''', 240 parts of cumene containing 0.1% by weight of ethylbenzene and having a purity of 99.8% and 26 parts of p-diisopropylbenzene were obtained respectively.

The amounts of benzene and propylene fed freshly to the reactor 1 were made substantially the same as in Example 1 (this same applies equally to the following Examples and Comparative Examples).

Comparative Example 1

In this example, the reaction temperature in the alkylation step (I) was higher than the specified reaction temperature.

Specifically, the procedure of Example 1 was repeated except that the reaction temperature was set at 110° C. in the alkylater 1, and at 74° C. in the transalkylater 2.

From the distillation steps 5' and 5''', 240 parts of cumene containing 0.22% by weight of ethylbenzene and having a purity of 99.7% and 26 parts of p-diisopropylbenzene were obtained, respectively.

It is clear from the results given in Table 1 that the amount of by-product ethylbenzene in this example was large.

Comparative Example 2

In this example, the reaction temperature in the transalkylation step (II) was higher than the specified limit.

Specifically, the procedure of Example 1 was repeated except that the reaction temperature was set at 79° C. in the alkylater 1 and at 95° C. in the transalkylater 2.

From the distillation steps 5' and 5''', 240 parts of cumene containing 0.29% by weight of ethylbenzene and having a purity of 99.6% and 26 parts of p-diisopropylbenzene were obtained, respectively.

It is clearly seen from the results given in Table 1 that the amount of by-product ethylbenzene was large.

EXAMPLE 3

In this example, m-diisopropylbenzene was also recovered as a product.

The reaction temperature was as shown in Table 1. 240 parts of cumene containing 0.07% by weight of ethylbenzene and having a purity of more than 99.9%, and 26 parts of m-diisopropylbenzene containing 4.1% by weight of trimethylindane were obtained as products.

Comparative Example 3

In this example, m-diisopropylbenzene was also recovered as a product as in Example 3. The transalkylation reaction temperature in step (II) was set at 95° C. which was higher than the specified limit.

The resulting cumene contained 0.23% by weight of ethylbenzene, and the resulting m-diisopropylbenzene contained as much as 15.3% by weight of trimethylindane.

EXAMPLE 4

167 Parts of benzene dehydrated and recycled from the distillation step 5 in FIG. 1 through line 15 and 170 parts of fresh benzene through line 6 were fed into an alkylater 1. The alkylater 1 was also charged with 105 parts of propylene containing 6 parts of propane through line 7 and 15 parts of the complex catalyst from the catalyst separator 3 through lines 10 and 21. The unreacted propane was discharged out of the reaction system through line 25. The reaction temperature in the alkylater 1 was maintained at 55° C.

The reaction product from the alkylater 1 was fed into a transalkylater 2 through line 26, and the transalkylater 2 was also charged with 86 parts of polyisopropylbenzenes such as m-diisopropylbenzene, p-diisopropylbenzene and triisopropylbenzene from distillation steps 5'' and 5'''' through lines 16 and 19, 210 parts of the complex catalyst from the catalyst separator 3 through lines 10 and 22, 0.4 part of substantially water-free hydrogen chloride through lines 9 and 24, and 0.45 part of aluminum trichloride intermittently through lines 8 and 23. The reaction temperature was maintained at 55° C. in the transalkylater 2.

The reaction product from the transalkylater 2 was fed into the catalyst separator 3 through line 27. The complex catalyst layer having a high specific gravity was recycled through line 10, and a portion (0.9 part) of it was discharged out of the reaction system through line 11. The catalyst component was completely removed from the oil layer in a neutralization tank, and 522 parts of the remainder was fed into the distillation step 5 through line 13.

In the distillation step, a distillation column for removal of ethylbenzene was not provided, and 240 parts of cumene containing 0.02% by weight of ethylbenzene and having a purity of more than 99.9% was obtained through line 17, and 26 parts of p-diisopropylbenzene containing 0.4% by weight of trimethylindane, through line 18. All (167 parts) of the benzene fraction was recycled to the alkylater 1 through line 15, and all (86 parts) of the remaining p-diisopropylbenzene, m-diisopropylbenzene and triisopropylbenzene fractions were recycled to the transalkylater 2 through lines 16 and 19. 2.6

Parts of high-boiling fractions were discharged through line 20.

The results are shown in Table 1.

Comparative Example 4

176 parts of benzene dehydrated and recycled from a distillation step 5 in FIG. 1 through line 15 and 171 parts of fresh benzene through line 6 were fed into an alkylater 1. The alkylater 1 was also charged with 106 parts of propylene containing 6 parts of propane through line 7, 105 parts of the complex catalyst from the catalyst separator 3 through lines 10 and 21, 0.2 part of substantially water-free hydrogen chloride gas intermittently through lines 9 and 28. The unreacted propane was discharged out of the reaction zone through line 25. The reaction temperature in the alkylater 1 was maintained at 55° C.

The reaction product from the alkylater 1 was fed into a transalkylater 2 through line 26. The transalkylater was also charged with 133 parts of polyisopropylbenzenes such as m-diisopropylbenzene, p-diisopropylbenzene and triisopropylbenzene recycled from the distillation step 5 through lines 16 and 19, 370 parts of the complex catalyst from the catalyst separator 3 through lines 10 and 22, 1.8 parts of substantially water-free hydrogen chloride through lines 9 and 24, and 2.3 parts of aluminum trichloride intermittently through lines 8 and 23. The reaction temperature in the transalkylater 2 was maintained at 55° C.

The reaction product from the transalkylater was fed into the catalyst separator 3 through line 27. The complex catalyst layer having a high specific gravity was recycled through line 10 and a portion (6.4 parts) of it was discharged out of the system through line 11. The catalyst component was completely removed from the oil layer in a neutralization tank 4, and 580 parts of the remainder was fed into the distillation step 5 through line 13.

In the distillation step, a distillation column for removal of ethylbenzene was not provided, and 240 parts of cumene containing 0.13% by weight of ethylbenzene and having a purity of 99.8% was obtained through line 17, and 26 parts of p-diisopropylbenzene containing 0.7% by weight of trimethylindane, from line 18. All (176 parts) of the benzene fraction was recycled to the alkylater 1 through line 15, and all (133 parts) of the remaining p-diisopropylbenzene, m-diisopropylbenzene and triisopropylbenzene fractions were recycled to the transalkylater 2 through lines 16 and 19. 4.3 Parts of high-boiling fractions were discharged through line 20.

The results are shown in Table 1.

EXAMPLE 5

188 Parts of benzene dehydrated and recycled from the distillation step 5 through line 15 and 157 parts of fresh benzene through line 6 were fed into an alkylater 1. The alkylater 1 was also charged with 91 parts of propylene containing 6 parts of propane through line 7, 15 parts of the complex catalyst from the catalyst separator 3 through lines 10 and 21, and 0.1 part of substantially water-free hydrogen chloride gas intermittently through lines 9 and 28. The unreacted propane was discharged out of the reaction system through line 25. The reaction temperature in the alkylater 1 was maintained at 75° C.

The reaction product from the alkylater 1 was fed into a transalkylater 2 through line 26. The transalkylater 2 was also charged with 141 parts of polyisopropylbenzenes such as m-diisopropylbenzene, p-diisopropylbenzene and triisopropylbenzene recycled from the distillation steps 5", 5''' and 5'''' through lines 16, 18 and 19, 156 parts of the complex catalyst from the catalyst separator 3 through lines 10 and 22, 0.3 part of substantially water-free hydrogen chloride through lines 9 and 24 and 0.55 part of aluminum trichloride intermittently through lines 8 and 23. The reaction temperature in the transalkylation 2 was maintained at 70° C.

The reaction product from the transalkylator 2 was fed into the catalyst separator 3 through line 27. The complex catalyst layer having a high specific viscosity was recycled through line 10, and a portion (1.0 part) of it was discharged out of the reaction system through line 11. The catalyst component was removed completely from the oil layer in a neutralization tank 4, and 571 parts of the remainder was fed into the distillation step 5 through line 13.

A distillation to column for removal of ethylbenzene was not particularly provided in the distillation step, and 240 parts of cumene containing 0.05% by weight of ethylbenzene and having a purity of more than 99.9% was obtained through line 17. All of the benzene fraction was recycled to the alkylater 1 through line 15, and all (141 parts) of the remaining p-diisopropylbenzene, m-diisopropylbenzene and triisopropylbenzene fractions were recycled to the transalkylater 2 through lines 16, 18 and 19. Two parts of high-boiling fractions were discharged through line 20.

The results are shown in Table 1.

EXAMPLE 6

60 Parts of benzene containing 49% by weight of cumene dehydrated and recycled from a distillation step 5 in FIG. 1 through line 15 and 13 parts of fresh benzene through line 6 were fed into an alkylater 1. The alkylater 1 was also charged with 14 parts of propylene through line 7, 2 parts of the complex catalyst from the catalyst separator 3 through lines 10 and 21 and 0.1 part of substantially water-free hydrogen chloride gas intermittently through lines 9 and 28. The reaction temperature in the alkylater 1 was maintained at 70° C.

The reaction product (87 parts) from the alkylator 1 was fed into a transalkylater 2 through line 26. The transalkylater 2 was also charged with 130 parts of cumene and polyisopropylbenzenes such as m-diisopropylbenzene, p-diisopropylbenzene and triisopropylbenzene recycled from distillation steps 5', 5" and 5'''' through lines 16, 17 and 19, 45 parts of the complex catalyst from the catalyst separator 3 through lines 10 and 22, 0.3 part of substantially water-free hydrogen chloride through lines 9 and 24 and 0.4 part by weight of aluminum trichloride intermittently through lines 8 and 23. The reaction temperature in the transalkylater 2 was maintained at 60° C.

The reaction product from the transalkylater was fed into the catalyst separator 3 through line 27. The complex catalyst layer having a high specific gravity was recycled through line 10, and a portion (0.8 part) of it was discharged out of the reaction system through line 11. The catalyst component was completely removed from the oil layer in a neutralization tank, and then 217 parts of the remainder was fed into the distillation step 5 through line 13.

In the distillation step, 26 parts of p-diisopropylbenzene was obtained from line 18 as a product. All of the benzene fraction was recycled to the alkylater. All (130 parts) of the remaining cumene fraction and the p-diisopropylbenzene, m-diisopropylbenzene and triisopropylbenzene fractions were recycled to the transalkylater 2 through lines 10, 17 and 19. 1.0 Part of high-boiling fractions were discharged through line 20.

The results are shown in Table 1.

EXAMPLE 7

54 Parts of benzene containing 57% by weight of cumene dehydrated and recycled from the distillation step 5 through line 15 and 13 parts of fresh benzene through line 6 were fed into an alkylater 1. The alkylater 1 was charged with 14 parts of propylene through line 7, 5 parts of the complex catalyst from the catalyst separator 3 through lines 10 and 21, and 0.1 part of substantially water-free hydrogen chloride gas intermittently through lines 9 and 28. The reaction temperature in the alkylater 1 was maintained at 70° C.

The reaction product from the alkylater 1 was fed into a transalkylater 2 through line 26. The transalkylater 2 was further charged with 92 parts of cumene and polyisopropylbenzenes such as m-diisopropylbenzene, p-diisopropylbenzene and triisopropylbenzene recycled from distillation steps 5', 5" and 5"" through lines 17, 18 and 19, 33 parts of the complex catalyst from the catalyst separator 3 through lines 10 and 22, 0.2 part of substantially water-free hydrogen chloride through lines 9 and 24 and 0.3 part of aluminum trichloride intermittently through lines 8 and 23. The reaction temperature in the transalkylater 2 was maintained at 60° C.

The reaction product from the transalkylater 2 was fed into the catalyst separator 3 through line 27. The complex catalyst layer having a high specific gravity was recycled through line 10, and a portion (0.6 part) of it was discharged out of the reaction system through line 11. The catalyst component was completely removed from the oil layer in a neutralization tank 4, and 173 parts of the remainder was fed into the distillation step 5 through line 13.

In the distillation step, 26 parts of m-diisopropylbenzene was obtained through line 16. All (54 parts) of the benzene fraction was recycled to the alkylator 1 through line 15, and all (92 parts) of the remaining cumene, p-diisopropylbenzene, m-diisopropylbenzene and triisopropylbenzene fractions were recycled to the transalkylator 2 through lines 17, 18 and 19. One part of high-boiling fractions were discharged from through line 20.

The results are shown in Table 1.

TABLE 1

| Example (Ex.) or Comparative Example (CEx.) | | | Ex. 1 | Ex. 2 | CEx. 1 | CEx. 2 | Ex. 3 | CEx. 3 | Ex. 4 | CEx. 4 | Ex. 5 | Ex. 6 | Ex. 7 |
|---|---|---|---|---|---|---|---|---|---|---|---|---|---|
| Reaction | | Alkylater | 79 | 80 | 110 | 79 | 77 | 79 | 55 | 55 | 75 | 70 | 70 |
| temperature (°C.) | | Transalkylater | 64 | 74 | 74 | 95 | 61 | 95 | 55 | 55 | 70 | 60 | 60 |
| Complex catalyst | M value ($\times 10^{-4}$ min$^{-1}$) | Alkylater | 190 | 80 | 4 | 11 | 180 | 11 | 210 | 305 | 180 | 210 | 220 |
| | | Transalkylater | 180 | 90 | 130 | 4 | 200 | 4 | 240 | 350 | 210 | 250 | 250 |
| | Concentration (parts/hr.) | Alkylater | 23 | 16 | 17 | 18 | 20 | 18 | 15 | 105 | 15 | 2 | 5 |
| | | Transalkylater | 250 | 219 | 205 | 182 | 195 | 182 | 210 | 370 | 156 | 45 | 33 |
| | Amount of AlCl$_3$ (parts/hr.) | Alkylater | 0.05 | 0 | 0 | 0.05 | 0 | 0.05 | 0 | 0 | 0 | 0 | 0 |
| | | Transalkylater | 0.6 | 0.6 | 1.0 | 0.7 | 0.6 | 0.7 | 0.45 | 2.3 | 0.55 | 0.4 | 0.3 |
| | Amount blown (parts/hr.) | | 1.1 | 0.3 | 1.9 | 0.6 | 1.0 | 0.6 | 0.9 | 6.4 | 1.0 | 0.8 | 0.6 |
| Fresh feeds | Propylene (parts/hr.) | | 99 | 100 | 100 | 103 | 99 | 103 | 99 | 100 | 85 | 14 | 14 |
| | Benzene (parts/hr.) | | 170 | 170 | 171 | 173 | 170 | 173 | 170 | 171 | 157 | 13 | 13 |
| Flow rate (parts/hr.) | line 26 (alkylater) | | 599 | 580 | 556 | 551 | 569 | 551 | 436 | 447 | 430 | 87 | 81 |
| | line 13 (feed to the distillation step) | | 776 | 755 | 711 | 701 | 742 | 701 | 522 | 580 | 571 | 217 | 173 |
| | line 15 (recycle benzene) | | 330 | 310 | 285 | 275 | 300 | 275 | 167 | 176 | 188 | 60 | 54 |
| | line 16 (recycle DIPB) | | 177 | 175 | 155 | 150 | 173 | 150 | 86 | 133 | 141 | 130 | 92 |
| Composition at line 13 (wt. %) | Benzene | | 42.6 | 41.1 | 37.4 | 35.5 | 40.2 | 35.6 | 31.9 | 30.3 | 32.7 | 7.8 | 7.9 |
| | Cumene | | 32.5 | 36.6 | 37.0 | 42.1 | 34.1 | 42.0 | 46.8 | 50.6 | 42.9 | 40.6 | 41.0 |
| | m-DIPB | | 14.8 | 13.5 | 15.1 | 11.5 | 16.2 | 11.3 | 13.8 | 10.9 | 14.4 | 28.0 | 27.2 |
| | p-DIPB | | 6.4 | 6.1 | 7.1 | 5.4 | 6.9 | 5.6 | 5.7 | 5.1 | 6.9 | 14.1 | 15.0 |
| | TIPB | | 1.5 | 0.8 | 1.1 | 1.4 | 1.5 | 1.6 | 1.0 | 0.7 | 1.4 | 7.6 | 7.7 |
| | Ethylbenzene | | 0.03 | 0.04 | 0.10 | 0.13 | 0.03 | 0.11 | 0.02 | 0.10 | 0.03 | 0.11 | 0.09 |
| | Trimethylindane | | 1.52 | 1.56 | 1.85 | 2.70 | 0.78 | 2.10 | 0.45 | 0.94 | 1.31 | 1.42 | 0.60 |
| Amount (parts/hr.) of high-boiling substances purged | | | 2.5 | 3.2 | 3.5 | 8.5 | 2.5 | 8.5 | 2.6 | 4.3 | 2.0 | 1.0 | 1.0 |
| Products | Cumene | Yield (parts/hr.) | 240 | 240 | 240 | 240 | 240 | 240 | 240 | 240 | 240 | — | — |
| | | Purity (%) | 99.9 ↑ | 99.8 | 99.7 | 99.6 | 99.9 ↑ | 99.7 | 99.9 ↑ | 99.7 | 99.9 ↑ | — | — |
| | | Concentration of EB (wt. %) | 0.06 | 0.10 | 0.22 | 0.29 | 0.07 | 0.23 | 0.02 | 0.17 | 0.05 | — | — |
| | p-DIPB | Yield (parts/hr.) | 26 | 26 | 26 | 26 | — | — | 26 | 26 | — | 26 | — |
| | | Purity (%) | 97.6 | 97.5 | 96.0 | 95.4 | — | — | 98.4 | 97.3 | — | 98.4 | — |
| | | Concentration of hexylbenzenes (wt. %) | 0.6 | 0.7 | 1.8 | 1.4 | — | — | 0.4 | 1.2 | — | 0.5 | — |
| | m-DIPB | Yield (parts/hr.) | — | — | — | — | 26 | 26 | — | — | — | — | 26 |
| | | Purity (%) | — | — | — | — | 95.3 | 83.5 | — | — | — | — | 97.5 |
| | | Concentration of TMI (wt. %) | — | — | — | — | 4.1 | 15.3 | — | — | — | — | 1.7 |
| Amount of AlCl$_3$ (per 1000 parts of DIPB in line 13) | | | 4 | 4.1 | 6.3 | 6.3 | 3.5 | 6.3 | 4.4 | 24.8 | 4.5 | 4.4 | 4.1 |
| AlCl$_3$ concentration (mole/l) | | Alkylater | 0.08 | 0.06 | 0.06 | 0.07 | 0.07 | 0.07 | 0.07 | 0.42 | 0.07 | 0.05 | 0.13 |
| | | Transalkylater | 0.59 | 0.53 | 0.53 | 0.50 | 0.50 | 0.50 | 0.69 | 1.06 | 0.52 | 0.40 | 0.40 |

What we claim is:

1. In a process for producing cumene and/or diisopropylbenzene which comprises, in combination, (I) an alkylating step of reacting benzene with propylene in the presence of a liquid aluminum chloride complex catalyst, (II) a transalkylating step of reacting the reaction product of step (I) containing the complex catalyst with recycle isopropylbenzene compounds from a distillation step (V) below in the presence of added fresh aluminum chloride and hydrogen chloride in a reaction zone different from the reaction zone of step (I), (III) a catalyst separating step of separating the liquid aluminum chloride complex catalyst from the transalkylation product of step (II) in a zone different from the zone of step (II) and recycling the separated catalyst to step (I) and/or step (II), (IV) a neutralization step of neutralizing the transalkylation product of step (III) with an alkali in a zone different from the zone of step (III), and (V) fractionally distilling the neutralization product of step (IV) in a zone different from the zone of step (IV) to recover the cumene fraction and/or the diisopropylbenzene fraction and recycling the remaining isopropylbenzene compounds to step (II); characterized in that (a) step (I) is carried out at a temperature of about 40° C. to about 85° C. while maintaining the activity coefficient (M) of the catalyst at about $10 \times 10^{-4}$ to about $300 \times 10^{-4}$ and the concentration of aluminum chloride in the system at 0.005 to 0.15 mole/liter, and (b) step (II) is carried out without removing the catalyst from the reaction product of step (I) and at a temperature of about 40° C. to about 75° C. in the presence of added fresh aluminum chloride in an amount of 2 to 20 parts by weight/hr per 1000 parts by weight/hr of diisopropylbenzene in the reaction system while maintaining the activity coefficient (M) of the catalyst in the system at about $30 \times 10^{-4}$ to about $300 \times 10^{-4}$ and the concentration of aluminum chloride in the system at 0.3 to 1 mole/liter.

* * * * *